United States Patent
Jellinggaard et al.

(10) Patent No.: US 11,983,873 B2
(45) Date of Patent: May 14, 2024

(54) METHOD, DEVICE AND SYSTEM FOR CORRELATING AT LEAST ONE ADDITIONAL 2D-IMAGE TO A 3D-REPRESENTATION OF AT LEAST A PART OF TOOTH

(71) Applicant: 3SHAPE A/S, Copenhagen K (DK)

(72) Inventors: Anders Robert Jellinggaard, Copenhagen K (DK); Christoph Vannahme, Holte (DK); Mike Van Der Poel, Rødovre (DK); Karl-Josef Hollenbeck, Copenhagen Ø (DK); Anders Gaarde, Søborg (DK); Mads Brøkner Christiansen, Farum (DK)

(73) Assignee: 3SHAPE A/S, Copenhagen K (DK)

( * ) Notice: Subject to any disclaimer, the term of this patent is extended or adjusted under 35 U.S.C. 154(b) by 640 days.

(21) Appl. No.: 17/253,710

(22) PCT Filed: Jun. 14, 2019

(86) PCT No.: PCT/EP2019/065747
§ 371 (c)(1),
(2) Date: Dec. 18, 2020

(87) PCT Pub. No.: WO2019/243202
PCT Pub. Date: Dec. 26, 2019

(65) Prior Publication Data
US 2021/0264600 A1    Aug. 26, 2021

(30) Foreign Application Priority Data

Jun. 21, 2018 (EP) .................................. 18179027

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0088* (2013.01); *A61B 34/74* (2016.02);
(Continued)

(58) Field of Classification Search
CPC ......... G06T 7/0014; G06T 2207/10048; G06T 2207/20024; G06T 2207/30036;
(Continued)

(56) References Cited

U.S. PATENT DOCUMENTS

| | | |
|---|---|---|
| 2003/0169913 A1 | 9/2003 | Kopelman |
| 2004/0029068 A1 | 2/2004 | Sachdeva et al. |

(Continued)

FOREIGN PATENT DOCUMENTS

| | | |
|---|---|---|
| CN | 103079494 | 5/2013 |
| CN | 106537225 | 3/2017 |

(Continued)

OTHER PUBLICATIONS

First Office Action issued in corresponding Chinese Patent Application No. 2019800548483, dated Aug. 31, 2021, with English Translation (16 pages).

(Continued)

*Primary Examiner* — Neil R McLean
(74) *Attorney, Agent, or Firm* — BUCHANAN INGERSOLL & ROONEY PC

(57) ABSTRACT

The present disclosure provides a computer-implemented method for correlating at least one infrared 2D-image to a 3D-representation of at least a part of a tooth displayed in a graphical user-interface, of a hand-held scanning device, on a screen, comprising the steps of: obtaining a first set of 2D-images of the at least part of the tooth; forming a 3D-representation of the at least a part of the tooth from the first set of 2D-images; displaying, in the graphical user-interface, the 3D-representation; obtaining a second set of (Continued)

2D-images, wherein the second set of 2D images are infrared 2D-images acquired within the at least part of the tooth; displaying, in the user-interface, at least one of the 2D-images from the second set of 2D-images; displaying, in the user-interface, a manipulator configured to change between 2D-images in the second set of 2D-images.

15 Claims, 3 Drawing Sheets

(51) Int. Cl.
*A61B 34/00* (2016.01)
*G06F 3/048* (2013.01)

(52) U.S. Cl.
CPC ...... *G06F 3/048* (2013.01); *A61B 2560/0487* (2013.01); *G06T 2207/10048* (2013.01); *G06T 2207/20024* (2013.01); *G06T 2207/30036* (2013.01)

(58) Field of Classification Search
CPC ....... G06T 19/00; A61B 5/0088; A61B 34/74; A61B 2560/0487; A61B 5/0062; A61B 2018/20353; G06F 3/048; A61C 13/0004; A61C 9/0053; G16H 30/00
USPC ........................................................ 382/128
See application file for complete search history.

(56) References Cited

U.S. PATENT DOCUMENTS

| | | |
|---|---|---|
| 2010/0121658 A1 | 5/2010 | Kaminski et al. |
| 2010/0281370 A1 | 11/2010 | Rohaly et al. |
| 2010/0283781 A1 | 11/2010 | Kriveshko et al. |
| 2016/0225151 A1 | 8/2016 | Cocco et al. |
| 2016/0295191 A1 | 10/2016 | Babayoff |
| 2017/0049330 A1 | 2/2017 | Kopelman |
| 2018/0028063 A1* | 2/2018 | Elbaz .................. H04N 13/271 |
| 2018/0101947 A9 | 4/2018 | Choi |

FOREIGN PATENT DOCUMENTS

| | | |
|---|---|---|
| CN | 107661159 | 2/2018 |
| JP | 2017221329 A | 12/2017 |
| WO | 2012000511 | 1/2012 |
| WO | 2017093563 A1 | 6/2017 |

OTHER PUBLICATIONS

Second Office Action issued in corresponding Chinese Patent Application No. 2019800548483, dated Jun. 2, 2022, with English Translation (16 pages).
International Search Report (PCT/ISA/210) dated Sep. 10, 2019, by the European Patent Office as the International Searching Authority for International Application No. PCT/EP2019/065747.
Written Opinion (PCT/ISA/237) dated Sep. 10, 2019, by the European Patent Office as the International Searching Authority for International Application No. PCT/EP2019/065747.
Office Action (Decision of Rejection) dated Nov. 1, 2022, by the Chinese Patent Office in corresponding Chinese Patent Application No. 201980054848.3, and an English Translation of the Office Action. (11 pages).

* cited by examiner

METHOD, DEVICE AND SYSTEM FOR CORRELATING AT LEAST ONE ADDITIONAL 2D-IMAGE TO A 3D-REPRESENTATION OF AT LEAST A PART OF TOOTH

FIELD OF THE INVENTION

This invention generally relates to a method, a device, and a system for correlating at least one additional 2D-image to a 3D-representation of at least a part of a tooth. More specifically, the invention relates to correlating the at least one additional 2D-image within the 3D-representation, wherein said 2D-image is recorded in a second recording mode that differs from a first recording mode being used to form the 3D-representation. Even more specifically, the invention relates to hand-held devices such as 3D-scanners used in dental healthcare.

BACKGROUND

Recording images using different recording modes is known in the field of dental healthcare. For example, 3D scanners are known to be configured for illuminating a tooth using both white light, for example from a white LED, and light of different color, for example from a red laser diode.

In some 3D scanners, 2D-images are thus acquired using white light illumination and red-light illumination.

The 2D-images acquired with the red-light illumination may be used for forming a 3D representation of a tooth, and the 2D-images acquired with the white light may be used in obtaining colors of the tooth. The colors from the 2D-images are associated to the surface of the 3D representation, for example by a color-mapping algorithm.

Thus, in presently known 3D scanners used in the dental healthcare, color-mapping is related to mapping of colors from 2D images to the outer surface of the 3D representation of for example a tooth. The color of the outer surface of a tooth represents the actual color of the tooth. By knowing the color of a tooth, that color may be matched to the color of a dental restoration, such as a crown, an inlay, an onlay and/or a bridge. Further, by knowing the color, one can distinguish between teeth and gingiva. Thus, color images of for example teeth are important not only for visualization of teeth but also for dental restorations.

Today, imaging and scanning of the outside surface of for example a tooth is well-established and can be achieved using various imaging techniques.

Further, bacteria and tooth decay can be imaged using violet or ultraviolet (UV) light, causing the bacteria and tooth material to fluoresce. The 2D-images acquired with UV-light is also known to be correlated to the outer surface of for example a tooth. Thus, an overlay of a 3D structure with fluorescence information is known in the art.

Even further, the inside of a tooth, i.e. approximal caries lesions in enamel, can be imaged using infrared (IR) light. More specifically, a 3D-representation of the inside of a tooth can be obtained by acquiring a set of 2D-images during IR-light illumination. The 3D-IR-representation of the inside of the tooth may be correlated to the outside of the tooth by various techniques. For example, the correlation of a 3D-IR-representation to a 3D-representation recorded using white light or red light can be achieved by matching features in the two representations.

Thus, today, correlation of one 3D-representation obtained in one recording mode within another 3D-representation obtained in a second recording mode is known in general.

Nevertheless, obtaining a first 3D-representation and correlating that within a second 3D-representation may require a long time to record and process, making it cumbersome to scan a mouth. Further, the information of the first 3D-representation within the second 3D-representation may be difficult and/or time-consuming to further analyze.

Thus, there is a need for a more efficient recording and correlation method of information within a tooth. Further, there is a need for providing information within a tooth such that this information can be further analyzed more easily.

SUMMARY

Disclosed herein is a method to provide a more efficient recording and correlation method of information within a tooth. Further disclosed is how to provide information within a tooth such that this information can be further analyzed more easily.

The below aspects of the invention address these objects.

In a first aspect, the present disclosure provides a computer-implemented method for correlating at least one additional 2D-image to a 3D-representation of at least a part of a tooth, comprising the steps of: obtaining a first set of 2D-images, wherein the first set of 2D-images are recorded in a first recording mode using a hand-held device; forming a 3D-representation of the at least a part of the tooth from the first set of 2D-images; defining a single 2D-representation-surface within the 3D-representation; obtaining at least one additional 2D-image, wherein the at least one 2D-image is recorded in a second recording mode different from the first recording mode using the hand-held device; and correlating the at least one 2D-image to the 3D-representation such that the at least one 2D-image lies in the single 2D-representation-surface in the 3D-representation. In this manner, the method may obtain a combined 2D/3D-representation. Particularly, the combined 2D/3D-representation may comprise the 3D-representation correlated with the at least one 2D-image only in the single 2D-representation-surface within the 3D-representation. In most embodiments, the at least one 2D-image lies inside the 3D-representation of the tooth, but the at least one 2D-image may in other embodiments lie on top of the 3D-representation of the tooth. Regardless of the orientation and position of the at least 2D-image, the 2D image is within the 3D-representation.

In a second aspect the present disclosure provides a processing unit for correlating at least one additional 2D-image to a 3D-representation of at least a tooth, wherein the processing unit is configured for performing the steps of: obtaining a first set of 2D-images, wherein the first set of 2D-images are recorded in a first recording mode using a hand-held device; forming a 3D-representation of the at least a part of the tooth from the first set of 2D-images; defining a single 2D-representation-surface within the 3D-representation; obtaining at least one additional 2D-image, wherein the at least one 2D-image is recorded in a second recording mode different from the first recording mode using the hand-held device; and correlating the at least one 2D-image to the 3D-representation such that the at least one 2D-image lies in the single 2D-representation-surface in the 3D-representation. In this manner, the method may obtain a combined 2D/3D-representation. Particularly, the combined 2D/3D-representation may comprise the 3D-representation correlated with the at least one 2D-image only in the single 2D-representation-surface within the 3D-representation.

In a third aspect, the present disclosure provides a 2D/3D-scanning-system for correlating at least one additional 2D-image to a 3D-representation of at least a part of a tooth, comprising: a hand-held device comprising: at least a first light source configured for transmitting light in a first optical domain and light in a second optical domain; a detector configured for recording 2D-images, wherein the hand-held device is configured for being operated in at least two recording modes: a first recording mode, wherein a first set of 2D-images are recorded onto the detector by illumination of light in the first optical domain, a second recording mode, wherein the at least one additional 2D-image is recorded onto the detector by illumination of light in the second optical domain; and a processing unit for correlating the at least one additional 2D-image to a 3D-representation of at least a tooth, wherein the processing unit is configured for performing the steps of: obtaining a first set of 2D-images, wherein the first set of 2D-images are recorded in the first recording mode using a hand-held device; forming a 3D-representation of the at least a part of the tooth from the first set of 2D-images; defining a single 2D-representation-surface within the 3D-representation; obtaining the at least one additional 2D-image, wherein the at least one 2D-image is recorded in the second recording mode different from the first recording mode using the hand-held device; and correlating the at least one 2D-image to the 3D-representation such that the at least one 2D-image lies in the single 2D-representation-surface in the 3D-representation. In this manner, the method may obtain a combined 2D/3D-representation. Particularly, the combined 2D/3D-representation may comprise the 3D-representation correlated with the at least one 2D-image only in the single 2D-representation-surface within the 3D-representation.

In a fourth aspect, the present disclosure provides a computer-implemented method for correlating at least one additional 2D-image to a 3D-representation of at least a part of a tooth displayed in a graphical user-interface on a screen, comprising the steps of: obtaining a first set of 2D-images, wherein the first set of 2D-images are recorded in a first recording mode using a hand-held device; forming a 3D-representation of the at least a part of the tooth from the first set of 2D-images in the graphical user-interface; defining a single 2D-representation-surface within the 3D-representation using a manipulator displayed in the graphical user-interface; obtaining at least one additional 2D-image, wherein the at least one additional 2D-image is recorded in a second recording mode different from the first recording mode using the hand-held device; and based on input as provided by the manipulator, correlating the at least one 2D-image to the 3D-representation such that the at least one 2D-image lies in the single 2D-representation-surface in the 3D-representation, thereby obtaining a combined 2D/3D-representation, the combined 2D/3D-representation comprising the 3D-representation correlated with the at least one 2D-image only in the single 2D-representation-surface within the 3D-representation.

In a fifth aspect, the present disclosure provides a computer-implemented method for correlating at least one additional 2D-image to a 3D-representation of at least a part of a tooth displayed in a graphical user-interface on a screen, comprising the steps of: obtaining a first set of 2D-images, wherein the first set of 2D-images are recorded in a first recording mode using a hand-held device; forming a 3D-representation of the at least a part of the tooth from the first set of 2D-images in the graphical user-interface; defining a single 2D-representation-surface within the 3D-representation; obtaining at least one additional 2D-image, wherein the at least one 2D-image is recorded in a second recording mode different from the first recording mode using the hand-held device; correlating the at least one 2D-image to the 3D-representation such that the at least one 2D-image lies in the single 2D-representation-surface in the 3D-representation, thereby obtaining a combined 2D/3D-representation, the combined 2D/3D-representation comprising the 3D-representation correlated with the at least one 2D-image only in the single 2D-representation-surface within the 3D-representation; re-defining the single 2D-representation-surface within the 3D-representation using a manipulator displayed in the graphical user-interface; and based on input as provided by the manipulator, re-correlating the at least one 2D-image to the 3D-representation.

Similar to the computer implemented method as described in the fifth aspect, the present disclosure provides a computer-implemented method for correlating at least one infrared 2D-image to a 3D-representation of at least a part of a tooth displayed in a graphical user-interface, of a hand-held scanning device, on a screen, comprising the steps of: obtaining a first set of 2D-images of the at least part of the tooth; forming a 3D-representation of the at least a part of the tooth from the first set of 2D-images; displaying, in the graphical user-interface, the 3D-representation; obtaining a second set of 2D-images, wherein the second set of 2D images are infrared 2D-images acquired within the at least part of the tooth; displaying, in the user-interface, at least one of the 2D-images from the second set of 2D-images; displaying, in the user-interface, a manipulator configured to change between 2D-images in the second set of 2D-images; based on input as associated to the manipulator, changing between the 2D-images in the second set of 2D-images until a desired 2D-image is displayed; and correlating the desired 2D-image to the 3D-representation.

All the aspects of the disclosure relate to obtaining a combined 2D/3D-representation of at least a part of a tooth. In preferred embodiments, the combined 2D/3D-representation may comprise the 3D-representation correlated with the at least one 2D-image only in the single 2D-representation-surface within the 3D-representation. Generally, a plane or the single plane of the 3D-representation may refer to a plane formed by one or more triangles, wherein the triangle(s) are defined between points in a point-cloud. By obtaining the at least one 2D-image only in the single 2D-representation-surface within the 3D-representation, i.e. specifically where the single 2D-representation-surface is defined according to the first aspect, the present invention provides a computer-implemented method, where it is possible to record only one 2D-image and correlate only that one 2D-image within the 3D-representation.

The herein disclosed method may therefore be much more efficient than recording a plurality of 2D-images in the second recording mode. Further, accordingly, the herein disclosed method may be much more efficient than correlating a plurality of 2D images.

Recording only one 2D-image and correlating only that one 2D-image in only the single 2D-representation-surface within the 3D-representation is advantageous because it allows for quick intra-oral scanning and/or examination of a patient thereby providing the patient with more comfort, at least because the patient does not need to have the mouth open for a long time. Further, recording only one 2D-image and correlating only that one 2D-image within the 3D-representation is advantageous because it allows the dental practitioner to observe only that one 2D-image in relation to the 3D-representation of the at least a part of the tooth.

For example, if a patient needs caries-examination in one tooth only, the dental practitioner may quickly record one 2D-image in the mouth, for example by recording only one 2D-image of the tooth using the second recording mode on the hand-held device, rather than recording a series of 2D-images per tooth. Hereafter, the single 2D-image is quickly correlated in the single 2D-representation-surface within the 3D-representation. In this manner, the practitioner may be allowed to further analyze, using various techniques, the combined 2D/3D-representation.

The combined 2D/3D-representation may in some embodiments be a representation as appearing on for example a display, such as a screen or touch-screen. Accordingly, the combined 2D/3D-representation may in some embodiments refer to a representation being two separate data-sets, for example two separate files, linked together by the correlation. The combined 2D/3D-representation may accordingly also be two separate representations, for example displayed separately in a user-interface, wherein the two separate displays are correlated to each other. For example, by inspecting the 2D representation, the correlation may allow the user of the user-interface to see where on the 3D-representation the 2D representation belongs. In other embodiments, the combined 2D/3D-representation may refer to a representation being a single data-set, for example obtained by correlating two separate data-sets and combining them into a single data file.

According to the present disclosure, it may also be possible to correlate more than one 2D-image within the 3D-representation. According to the present invention, all these 2D-images lie only in the defined single 2D-representation-surface within the 3D-representation.

Thus, when obtaining more than one 2D-image only in the single 2D-representation-surface within the 3D-representation, i.e. specifically where the single 2D-representation-surface is defined according to the first aspect, the present invention provides a computer-implemented method, where it is possible to record more than one 2D-image and correlate these 2D-images within the 3D-representation.

Since the 2D-images all lie only in a single 2D-representation-surface, all the 2D-images form only a 2D image within the 3D-representation. Accordingly, the present invention does not provide a combined 3D/3D-representation, where for example a first 3D-representation is correlated with multiple 2D-images that form another 3D-representation.

Correlating more than one 2D-image to a single 2D-representation surface may be much faster than correlating more than one 2D-image to multiple 2D-representation surfaces.

The herein disclosed method may therefore be much more efficient than recording a plurality of 2D-images and correlating these to multiple 2D-representation-surfaces within the first 3D-representation.

Recording more than one 2D-image and correlating these 2D-images in only the single 2D-representation-surface within the 3D-representation is further advantageous because it allows for quick intra-oral scanning and/or examination of a patient thereby providing the patient with more comfort, at least because the patient does not need to have the mouth open for a long time. Further, recording more than one 2D-image and correlating these 2D-images in only the single 2D-representation-surface within the 3D-representation is advantageous because it allows the dental practitioner to observe only 2D-images in one surface in relation to the 3D-representation of the at least a part of the tooth.

For example, if a patient needs caries-examination for all the teeth, the dental practitioner may quickly record more than one 2D-image in the mouth, for example by recording only one 2D-image per tooth using the second recording mode on the hand-held device, rather than recording a series of 2D-images per tooth. Hereafter, these 2D-images are quickly correlated in the single 2D-representation-surface within the 3D-representation. In this manner, the practitioner may be allowed to further analyze, using various techniques, the combined 2D/3D-representation.

Further details of the disclosure are described in the following.

BRIEF DESCRIPTION OF THE DRAWINGS

The above and/or additional objects, features and advantages of the present disclosure, will be further described by the following illustrative and non-limiting detailed description of embodiments of the present disclosure, with reference to the appended drawing(s), wherein.

DETAILED DESCRIPTION

Figure 1:
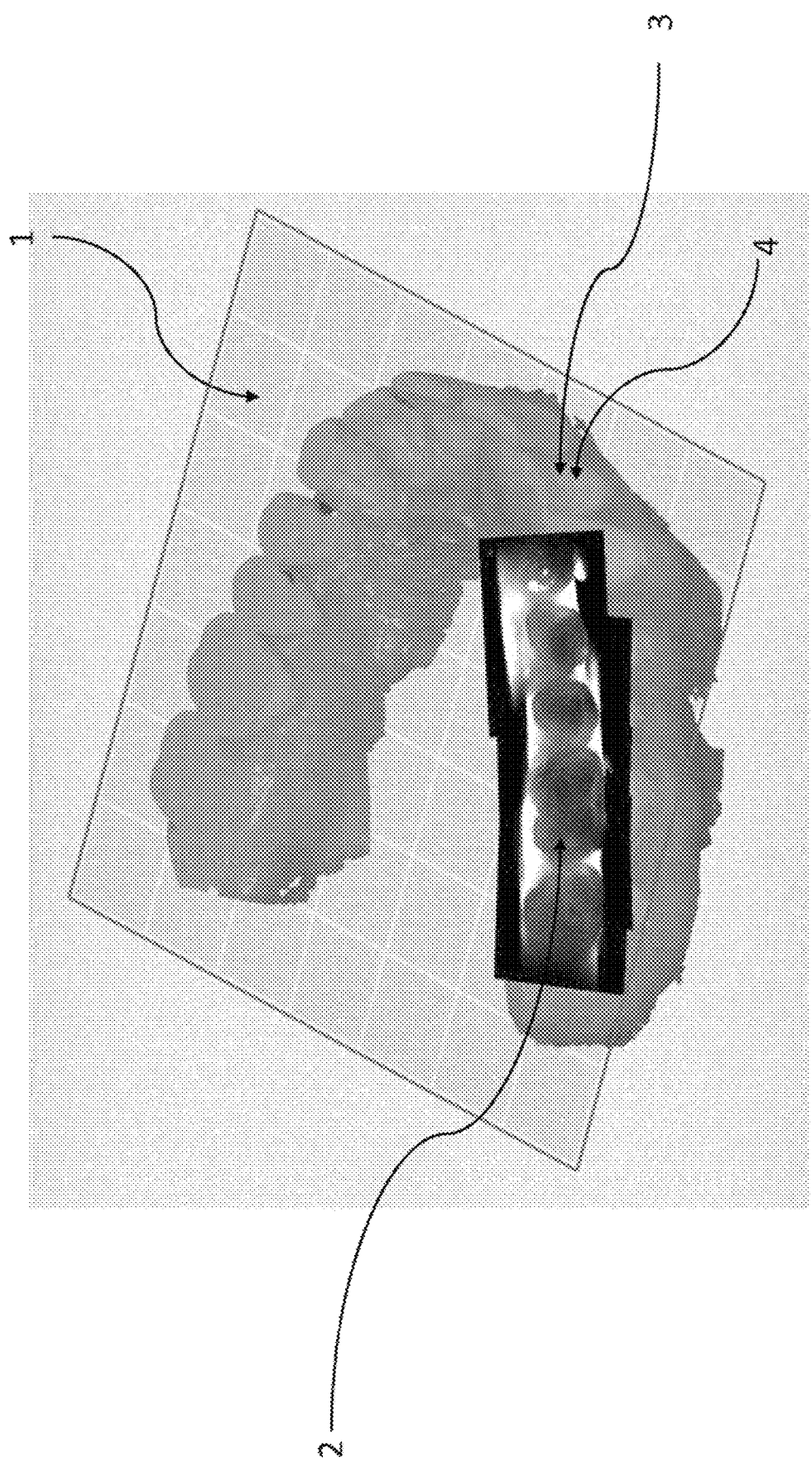
FIG. 1 shows an example of more than one 2D-image correlated to a 3D-representation.

Computer-Implemented Method
Defining the Single 2D-Representation-Surface

In one embodiment of the computer-implemented method, the step of defining the single 2D-representation-surface is performed before the step of correlating the at least one additional 2D-image to the 3D-representation.

In another embodiment of the computer-implemented method, the step of defining the single 2D-representation-surface is performed after the step of correlating the at least one additional 2D-image to the 3D-representation. For example, in some embodiments, the single 2D-representation-surface may first be defined before the step of correlating the at least one additional 2D-image to the 3D-representation, where-after the single 2D-representation-surface may be re-defined. This may allow for various options for the representation of the at least one 2D-image within the 3D-representation.

In a preferred embodiment, the single 2D-representation-surface is a planar surface. Such a representation-surface may provide a rapid correlation of the at least one additional 2D-image to the 3D-representation. Furthermore, when viewed from a perspective, the planar surface may show details that can all be seen from a single perspective.

In another preferred embodiment, the single 2D-representation-surface is a curved surface. Such a representation-surface may for example be used when the at least one additional 2D-image is a set of 2D-images, each of the 2D-images acquired at different focal planes. In such a case, the different focal planes may not necessarily form a single focal plane, and thus may not necessarily lie in a corresponding single planar 2D-representation plane in the 3D-representation. Accordingly, if the different focal planes correspond to a single 2D-representation-surface, an optimal surface may be curved.

On the other hand, if the different focal planes do not correspond to a single 2D-representation-surface, it may be possible to define a single planar 2D-representation-surface as described before that best matches all the different focal planes, for example by a least square method. Also, it may be possible to project the set of 2D-images to a single planar 2D-representation surface.

In most embodiments, the single 2D-representation-surface is an intersection-surface through the 3D-representation of the at least a part of the tooth. For example, if a focal plane within the tooth or a part thereof, i.e. related to the physical world, corresponds to a single 2D-representation-surface within the 3D-representation, i.e. related to the representation-world, then this embodiment corresponds to a situation where the at least one additional 2D-image is acquired within the tooth. This may be possible using for example infrared or x-ray imaging techniques.

In one embodiment, the single 2D-representation-surface is re-defined, for example, the single 2D-representation may be moved from its initial position, based on input from a user-interface or input from the hand-held device. For example, in relation to input from a user-interface, the input may be provided after a user clicks on a touch-screen. In relation to input from the hand-held device, the input may be provided after a user clicks and/or moves the hand-held device.

In a preferred embodiment, the step of defining the single 2D-representation-surface is based on spanning a fitting-surface relative to the 3D-representation of at least part of the tooth, preferably relative to the cusp of the 3D-representation of at least said tooth. Such a definition-step is preferably automatic. For example, the cusp of the 3D-representation of at least said tooth may automatically be found using a method that relies on estimating an occlusal direction based on scan direction, and from the occlusal direction, finding local maxima corresponding to the cusps of the teeth. Such a method may be an iterative process.

As described, the above embodiment may depend on determining properties of the 3D-representation, such as the cusp(s). The fitting-surface may then be determined by a least-square algorithm, for example in relation to the determined properties of the 3D-representation.

In another embodiment, the step of defining the single 2D-representation-surface is based on selecting a focal plane within the first set of 2D-images. For example, the step of selecting the focal-plane may be based on input from a user-selected 2D image. In other words, the focal plane may be manually selected based on viewing the first set of 2D-images. In another example, the step of selecting the focal plane may be automatic, such as selected based on a selection-algorithm, for example a focusing measure of the first set of 2D-images, or at least a part of the first set of 2D-images, for example based on a part an image within the first set of 2D-images.

Obtaining at Least One Additional 2D-Image

In one embodiment, the step of obtaining the at least one additional 2D-image is based on the at least one additional 2D-image being recorded after and/or before recording at least one 2D image in the first set of 2D-images being recorded in the first recording mode. For example, all the teeth in a mouth may be scanned in the first recording mode. Hereafter, all the teeth may be 2D-imaged in the second recording mode, for example by acquiring a single 2D-image for each of the teeth. This process may also be the other way around. In another example, all the teeth may be scanned and imaged in a process where each tooth is firstly partly scanned using the first recording mode, secondly 2D-imaged using the second recording mode, and thirdly partly scanned again using the first recording mode. Each tooth may then be scanned and 2D-imaged in a process where the recording mode is alternating between the first and the second recording mode, for example as described above, or in many steps, such that the above process is repeated several times, thereby recording more than a single 2D-image in the second recording mode for each tooth.

In a second embodiment, the at least one additional 2D-image is a second set of 2D-images, such as a focus-stack of 2D-images recorded perpendicular to a single 2D-physical-surface corresponding to the single 2D-representation-surface, and/or such as a series of 2D-images recorded along a single 2D-physical-surface corresponding to the single 2D-representation-surface. As described above, recording more than a single 2D-image may be realized by recording a set of 2D images for one or more teeth, for example alternating between recoding in the first and the second recording mode during scanning, thereby recording a focus stack for each tooth. The series of 2D-images along the single 2D-physical surface may also be recorded by moving the hand-held device along a path of all the teeth in the mouth. The user may record the series of 2D-images along the single 2D-physical surface by physically moving the scanner over the all the teeth in the mouth, for example with a substantial fixed distance to the teeth. Alternatively, the user may record the series of 2D-images along the single 2D-physical surface by physically moving the scanner over the all the teeth in the mouth, for example with a non-fixed distance to the teeth, and then rely on a projection algorithm which then projects the series of 2D-images into the single 2D-representation surface.

In another embodiment, the single 2D-representation surface is fitted to the position and orientation of the images in the second set of 2D-images, preferably when the set of 2D-images is recording along a path which defines a surface. The position and orientation of the images may be derived from the hand-held device, for example using motion and/or position sensors residing inside the hand-held device. In this embodiment, the fitting may be done algorithmically.

As described above, more than a single 2D-image is possible to obtain according to the present disclosure. Accordingly, in one embodiment, the step of obtaining the at least one additional 2D-image is based on filtering the second set of 2D-images. For example, a selection algorithm may be applied to the set of 2D-images to select the single 2D-image. In some embodiments, filtering may be various filtering techniques such as noise filtering, and/or color filtering.

In another embodiment, the step of obtaining the at least one additional 2D-image is based on the at least one additional 2D-image being recorded when the hand-held device is focused within a selected distance from a single 2D-physical surface corresponding to the single 2D-representation-surface. For example, the selected distance may be determined using an optical focusing system in the hand-held device.

In yet another embodiment, the step of obtaining the at least one additional 2D-image is based on the at least one additional 2D-image being recorded when the hand-held device is focused on at least a part of a tooth within a selected angular position at a single 2D-physical surface corresponding to the single 2D-representation-surface. For example, the selected angular position may be determined using a gyroscopic system in the hand-held device.

Correlating the at Least One Additional 2D-Image to the 3D-Representation

In a preferred embodiment, the step of correlating the at least one additional 2D-image to the 3D-representation is based on projecting the at least one additional 2D-image to the single 2D-representation-surface within the 3D-representation.

In yet another preferred embodiment, the step of correlating the at least one additional 2D-image to the 3D-representation further comprises obtaining a second set of 2D-images in the second recording mode and stitching said 2D-images in the 2D-representation-surface using an image fusion algorithm. As previously described, a set of 2D-images, or a series 2D-images, may be recorded along a single 2D-physical surface by moving the hand-held device along all the teeth in the mouth.

First and Second Recording Mode

In one embodiment, the first recording mode is based on illuminating the tooth with light in the visible domain, preferably with one or more wavelengths in the range between 400 nm to 700 nm, more preferably in the range between 400 nm to 600 nm. In some embodiments, the one or more wavelengths is in the range between 600 nm to 700 nm. For example, a laser diode operating at around 682 nm may be used to provide 3D information from the first set of 2D-images for the 3D-representation of at least the part of the tooth, i.e. for providing geometry of at least part of the tooth. Another wavelength range, for example originating from a white LED, may be used to provide only color information of at least the part of the tooth and overlay that color information on the geometry of the 3D-representation. In preferred embodiments, the one or more wavelengths in the visible domain, for example centered around 550 nm, may be used to provide both 3D information and color information from the first set of 2D-images for the 3D-representation of at least the part of the tooth.

In a second embodiment, the first recording mode comprises a step of illuminating the tooth with light in the ultraviolet (UV) domain, preferably light below 400 nm, such as between 200 nm and 400 nm, such as around 400 nm or around 300 nm. Light in the UV domain is suitable for providing information about surface caries on teeth. In a preferred embodiment, the first recording mode may be an alternation between recoding in the visible domain and the UV domain. Light in the visible domain may be used primarily in forming the 3D-representation, comprising geometry information and/or color information, whereas light in the UV domain may be used primarily in forming additional information to the 3D-representation, such as surface caries or dental plaque of at least a part of the tooth or gingiva. In some embodiments, light in the UV domain may be used primarily in forming the 3D-representation, particularly for providing only geometry information. In some preferred embodiments, light in the UV domain may be used primarily in forming the 3D-representation, particularly for providing both geometry information and additional information, such as surface caries of at least a part of the tooth.

In a preferred embodiment, the second recording mode is based on illuminating the tooth with light in the infrared (IR) domain, preferably with one or more wavelengths in the range between 700 nm to 2500 nm, more preferably in the range between 800 nm to 1000 nm, most preferably around 850 nm. Light in the IR domain is suitable for providing information about caries inside the teeth. In a more preferred embodiment, the first recording mode and the second recording mode are alternating in scanning operation of at least the part of the tooth. In a most preferred embodiment, the first recording mode may be in the visible domain and the second recording mode may be in the IR domain. Thereby, information related to color, geometry, and caries inside at least the tooth may be provided. In another most preferred embodiment the first recording mode may be both in the visible domain and the UV domain, whereas the second recording mode may be in the IR domain. UV light may provide information related to color, geometry, and caries outside of at least the tooth.

In another embodiment, the second recording mode is based on illuminating the tooth with light in the visible domain, preferably with one or more wavelengths in the range between 600 nm to 700 nm. This wavelength range may in some cases provide caries information of inside the teeth. Thus, in a possible embodiment, the first set of 2D images is recorded in the visible domain, for example the 400-600 nm range, and the second set of 2D images is also recorded in the visible domain, but for example in the 600-700 nm range. In this embodiment, it may in one embodiment be possible to change between the first and the second recording mode by wavelength-tuning a light source, such as a tunable laser.

Displaying the Combined 2D/3D-Representation

In most embodiments, the combined 2D/3D-representation is displayed on a screen. This allows a dental practitioner to observe the 2D/3D-representation as provided by using the hand-held device inside the oral cavity. The combined 2D/3D representation according to the present disclosure is efficiently obtained. When displayed on a screen, the present invention provides information about at least the tooth in a comprehensive manner that is visually understandable.

More importantly, when providing the combined 2D/3D-representation, it may be possible to easily derive measurable information about at least the tooth. For example, an image-based metric of the caries of at least the tooth that is based on both the 3D-representation recorded in the first recording mode, and the 2D-representation recorded in the second recording mode, may be more precise than only relying on purely 2D-information that is not linked to 3D-information. Providing an image-based metric of the caries based on the combined 2D/3D-representation may be a way to analyze the combined 2D/3D-representation. In general, when providing the combined 2D/3D-representation, image-based metrics of at least part of the tooth are able to be implemented in an easy manner, which allows a dental practitioner to obtain information about at least the tooth. Specific examples of such information may be related to caries and/or cracks.

Processing Unit

In a preferred embodiment, the processing unit is configured for performing the computer implemented method according to the first aspect.

The features of the method as described in this disclosure may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

2D/3D-Scanning-System

The Processing Unit

In one embodiment of the 2d/3D-scanning system, the processing unit is located externally to the hand-held device, such as located in a separate computer. In another embodiment of the 2d/3D-scanning system, the processing unit is located internally in the hand-held device. In some embodiments, the processing unit is shared between the hand-held device and an external device. Thus, in some embodiments the processing unit may be two or more processing units. Thus, in further embodiments, there may be a processing unit in both the hand-held device and externally to the hand-held device.

The First and Second Optical Domain

In one embodiment, the first optical domain is in the visible domain, preferably with one or more wavelengths in the range between 400 nm to 700 nm, more preferably in the range between 400 nm to 600 nm. Examples of a first light source that transmits light in the visible domain ranges from white light emitting diodes (LEDs) to white laser sources.

In a second embodiment, the first optical domain is in the ultraviolet or violet domain.

In a preferred embodiment, the second optical domain is in the infrared domain, preferably with one or more wavelengths in the range between 700 nm to 2500 nm, more preferably in the range between 800 nm to 1000 nm, most preferably around 850 nm.

In another preferred embodiment, the second optical domain is in the visible domain, preferably with one or more wavelengths in the range between 600 nm to 700 nm.

Further details of the various optical domains and combinations thereof can be found in relation to the computer-implemented method.

The at Least First Light Source

In one embodiment, the at least first light source is a first light source and a second light source. For example, the first light source may be a white LED and the second light source may be an IR light source. As described in relation to the first embodiment, the at least first light source may in some embodiments be a wavelength tunable light source.

The First and Second Recording Mode

In preferred embodiments, the at least one additional 2D-image is recorded after and/or before at least one 2D image in the first set of 2D-images being recorded in the first recording mode. Various combinations of recording processes have been described in relation to the computer-implemented method.

In relation to the 2D/3D-scanner system, and as previously described, the hand-held device is configured for being operated in at least two recording modes: a first recording mode, wherein a first set of 2D-images are recorded onto the detector by illumination of light in the first optical domain, and a second recording mode, wherein the at least one additional 2D-image is recorded onto the detector by illumination of light in the second optical domain.

Many options are possible for operating the hand-held device in the at least two recording modes.

In one embodiment, the first recording mode is provided by the hand-held device further comprising a first removable tip, which optically connects to the at least first light source, thereby guiding the light from the at least first light source towards at least a part of the tooth.

In another embodiment, the second recording mode is providing by the hand-held device further comprising a second removable tip, replacing the first removable tip, which optically connects to the at least first light source, thereby guiding the light from the at least first light source towards at least a part of the tooth.

In a preferred embodiment, the at least first light source is separately located from the first removable tip. As previously described, the at least first light source may be a first light source and a second light source.

In some embodiments, the at least first light source is located in or on the first removable tip and/or the second removable tip. For example, the first removable tip may comprise a first light source. Alternatively, and/or additionally, the second removable tip may comprise a second light source.

In a preferred embodiment, the first removable tip comprises no first light source, and the second removable tip comprises the second light source. The first light source may for example reside inside the handheld device, such that the light from the first light source is only guided via the first removable tip, for example by a mirror located in the first removable tip. The second light source may for example be an IR light source placed on/in the second removable tip.

In a more preferred embodiment, the first removable tip comprises no first light source, and the second removable tip comprises no second light source. Both the first and second light source may for example reside inside the handheld device, such that both the light from the first and second light source is only guided via the first removable tip and the second removable tip, respectively.

In some embodiments, the first removable tip comprises the first light source, and the second removable tip comprises the second light source. Both the first and second light source may for example reside in or on the first removable tip and the second removable tip, respectively.

Extended Depth-of-Field Imaging Setup

In one embodiment, the hand-held device further comprises an aperture optically connected to the detector, the aperture comprising an outer annular disc configured for blocking the light in the second optical domain, such that the at least one additional 2D-image is recorded with extended depth-of-field compared to the first set of images recorded in the first recording mode.

This embodiment would be able to for example provide the at least one additional 2D-image, preferably in the IR-domain, would show more details of for example caries inside the teeth along the direction of acquisition. By extending the depth-of-field, no focus stack of 2D-images within a tooth would be needed, and consequently no selection of a single 2D image within such a focus stack would be needed. Thus, extending the depth-of-field would provide a faster recording and forming of the combined 2D/3D-representation of at least a tooth.

Graphical User-Interface

Manipulator and Correlation

As previously described for the user-interface, the manipulator is configured to change between 2D-images in the second set of 2D-images. Further, based on input as associated to the manipulator, one can change between the 2D-images in the second set of 2D-images until a desired 2D-image is displayed. Once this is achieved, the user observes, in the user-interface, how the desired 2D image is correlated to the 3D-representation as also displayed. The correlation of the desired 2D image to the 3D-representation itself needs not to be calculated once the manipulator is positioned. For example, in the second set of 2D-images, one or more of the 2D-images may have been correlated to the 3D representation before they are displayed in the user-interface. One advantage of having the manipulator is to see wherein or whereon the 3D-representation the selected 2D image belongs. Another advantage of the manipulator is to display a correlated image once a location on the 3D-representation is defined.

In some embodiments, the correlation of the desired 2D-image to the 3D-representation may be calculated once the manipulator is positioned, for example on the 3D-representation. In other words, the correlation may only be calculated once the manipulator is positioned at a desired location on the 3D-representation. To position the manipulator at a desired location on the 3D-representation, the user-interface may in one embodiment be configured such that the manipulator can be moved relative to a fixed 3D-representation. In another embodiment, to position the manipulator at a desired location on the 3D-representation, the user-interface may be configured such that the 3D-representation is moved relative to a fixed manipulator. Moving the manipulator or the 3D-representation may in some embodiments be done using a handheld scanning device.

In preferred embodiments of the graphical user-interface, the manipulator displayed in the graphical user-interface is a scrollbar.

The manipulator may however also be the single 2D-representation surface itself. In such a case, the user may for example click on the single 2D-representation surface, and then move the single 2D-representation surface, for example by moving a cursor, by a touch-input on a screen, or by using the hand-held device.

In relation to positioning the manipulator, it follows from the above, that associated to the manipulator, i.e. the position of the manipulator, the user may specify where the user wants to see a correlation between a desired 2D-image and the 3D-representation or the other way around. Since the desired 2D-image is an infrared 2D-image acquired within the at least part of the tooth, the user is provided with the relationship between image-information inside the tooth and surface geometry-information of the tooth. This has the advantage that if the image information inside the tooth relates to carries, then the user can identify in which tooth the carries belongs, and then further, the user can identify where inside the tooth the carries is present.

In one embodiment, the step of correlating the desired 2D-image to the 3D-representation is based on comparing information in the first set of images with information in the second set of images. For example, the information in the first set of images, i.e. recorded with white visible light, may be features of the images, such as edges, for example provided by applying an edge-detection algorithm to the images. The information in the second set of images, i.e. recorded with infrared light, may also be similar features of the images, such as the edges.

In a preferred embodiment, the information is related to the acquisition-time of the images. This is advantageous over for example feature-detection, because the acquisition time is always present, but this is not always true for image-features such as edges. To compare the acquisition-times of the different set of images, a scanner acquiring the images and communicating with the user-interface, may in one embodiment be configured to rapidly shift between acquisition modes, for example between a white light illumination/acquisition mode and an infrared illumination/acquisition mode.

In one embodiment, the step of correlating the desired 2D-image to the 3D-representation is represented in the user-interface such that only the desired 2D-image is shown in relation to the 3D-representation of the at least a part of the tooth. In other words, when the user has selected the desired 2D-image, the user is able to observe whereon or wherein the desired 2D-image relates to the 3D-representation. For example, when the desired 2D-image inside the tooth is selected, using the manipulator, the same tooth may be represented as a separate 3D-representation, and a correlation-indicator may for example show the location of where the desired 2D-image relates and/or correlate to the 3D-representation. As previously explained, this has the advantage that if the image information inside the tooth relates to carries, then the user can identify in which tooth the carries belongs, and then further, the user can identify where inside the tooth the carries is present.

In another embodiment, the step of correlating the desired 2D-image to the 3D representation is represented in the user-interface as a combined 2D/3D-representation. As just described, the combined 2D/3D-representation may be two separate representations, for example displayed separately in a user-interface, wherein the two separate displays are correlated to each other. For example, by inspecting the 2D representation, the correlation may allow the user of the user-interface to see where on the 3D-representation the 2D representation belongs.

In yet another embodiment, the combined 2D/3D-representation comprises two separate datasets linked together by the correlation such that the combined 2D/3D-representation further comprises two separate representations.

However, in some embodiments the combined 2D/3D-representation may refer to a single representation, where both the 3D-representation and the 2D-image are simultaneously displayed. This has the advantage that the user needs not to look at two separate representations in the user-interface at the same time.

In other embodiments, the combined 2D/3D representation comprises a single dataset obtained by correlating two separate datasets. A first dataset may originate from the first set of 2D-images, and a second dataset may originate from second set of 2D-images, the i.e. the infrared 2D-images.

In one embodiment, the step of forming the 3D-representation is such that each tooth or the at least part of the tooth in the 3D-representation uniquely identifies a second set of images belonging to the respective tooth or the at least part of the tooth. In this manner, when a tooth or the at least part of the tooth in the 3D-representation is selected in the user-interface, for example using a correlation-indicator on the 3D-representation, the second set of 2D-images acquired within the tooth or within the at least part of the tooth is displayed as an image-by-image in the user-interface. As previously described for a correlation-indicator, the role of the correlation-indicator is to show the location of where the desired 2D-image relates and/or correlate to the 3D-representation—either from the 3D-representation and to the 2D-image or the other way around. In this embodiment, the user may for example select a tooth and by inspection of the corresponding 2D infrared images determine whether there is carries inside a tooth or between the teeth.

In some embodiments, the second set of 2D-images is a focus-stack of 2D-images recorded along a perpendicular axis with respect to a single 2D-physical-surface. This may for example allow a user to check for carries within a tooth at various distances from the cusps.

In other embodiments, the second set of 2D-images is a focus-stack of 2D-images recorded along a single 2D-physical surface. Preferably, the second set of 2D-images is both a focus-stack along a perpendicular axis with respect to a single 2D-physical-surface and along the same single 2D-physical surface. In this manner, the user is presented with most information of carries within a set of teeth.

In a preferred embodiment, the manipulator displayed in the graphical user-interface is a scrollbar and/or a location-indicator to show images from selected positions and/or orientations inside a tooth or a part thereof.

In another embodiment, the manipulator displayed in the graphical user-interface is based on clicking on the 2D-image and wherein the desired image is obtained by moving a cursor, by touch input on the screen, or by using the hand-held scanning device.

In some embodiments, the step of obtaining a second set of 2D-images is based on filtering the second set of 2D images. For example, if a set of infrared 2D-images are acquired as a focus stack, the filter may be configured to select only a part of them, for example based on image quality of location. In this manner, the correlation may not require correlating all of the 2D-images to the 3D-representation, and therefore a more efficient correlation may be provided.

In a preferred embodiment, the infrared images are obtained by, in the user-interface, selecting that the handheld scanning device is operating with one or more wavelengths in the range between 700 nm to 2500 nm. This may allow the user to manually acquire an infrared image, for example when the handheld scanner is positioned above a specific tooth of interest.

As previously described, in most embodiments, a hand-held scanning device is in communication with the graphical user-interface as described above.

Example 1—More than One 2D-Image Correlated to a 3D-Representation

FIG. 1 shows an example of a single 2D-representation-surface 1 with a set of additional 2D-images 2 correlated to a 3D-representation 3 of a tooth 4, obtained using the herein disclosed computer-implemented method. The single 2D-representation-surface 1 is within the 3D-representation 3 of all the teeth 4 present in a lower jaw. In this example, the single 2D-representation-surface 1 is a planar surface, particularly an intersection-surface that passes through approximately the center of the teeth 4. As shown in FIG. 1, the set of 2D-images 2 are in this example six 2D-images, which all lie in the single 2D-representation-surface. The six 2D-images are stitched together using an image fusion algorithm. Further, the set of 2D-images are recorded in the second recording mode that is based on illuminating the tooth with light in the infrared domain, in this case a wavelength around 850 nm.

Example 2—More than One 2D-Image Correlated to a 3D-Representation

Figure 2:
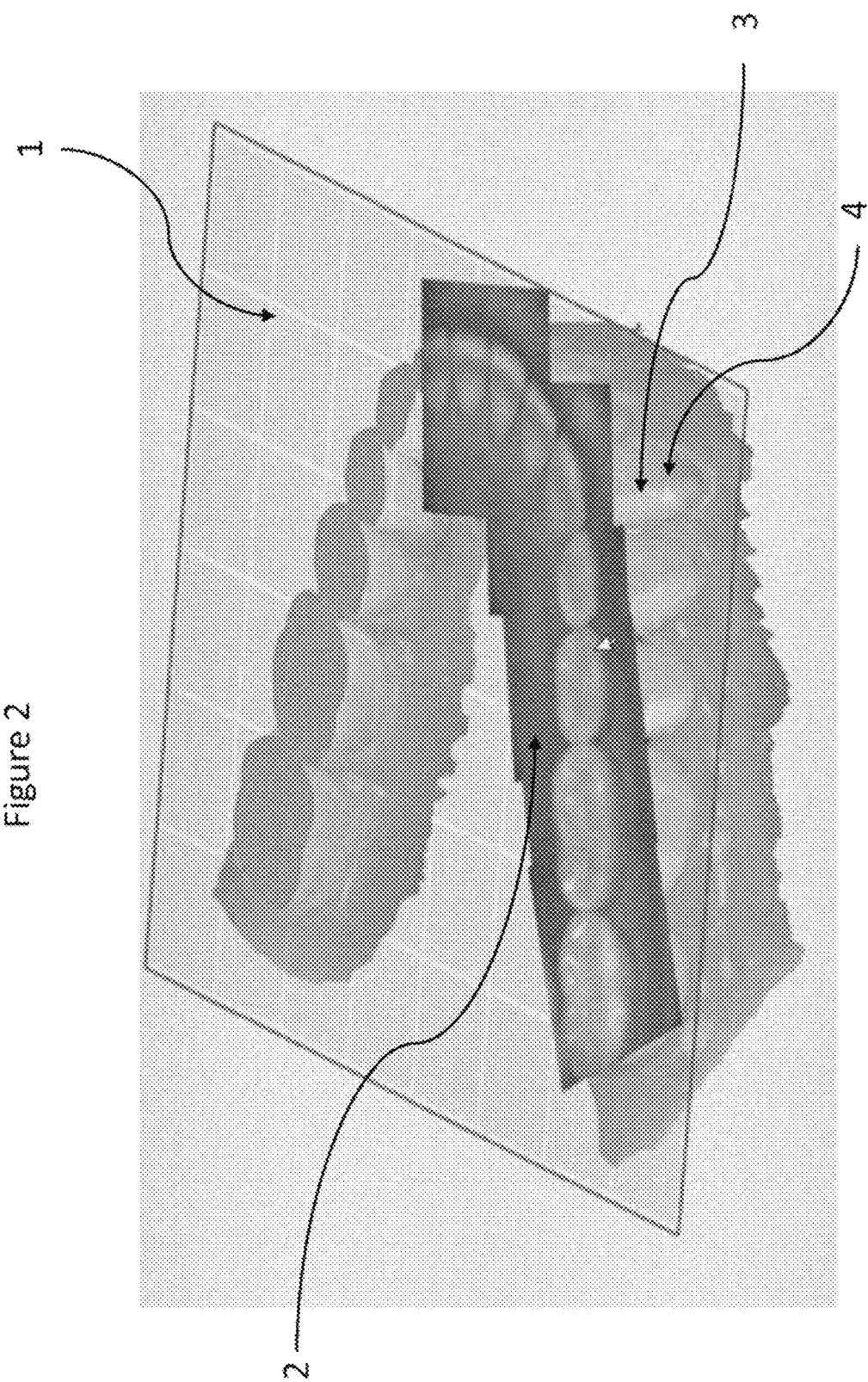
FIG. 2 shows another example of more than one 2D-image correlated to a 3D-representation.

FIG. 2 shows an example of a single 2D-representation-surface 1 with a set of additional 2D-images 2 correlated to a 3D-representation 3 of a tooth 4, obtained using the herein disclosed computer-implemented method. The single 2D-representation-surface 1 is within the 3D-representation 3 of all the teeth 4 present in a lower jaw. In this example, the single 2D-representation-surface 1 is a planar surface, particularly an intersection-surface that passes through approximately the center of the teeth 4. As shown in FIG. 2, the set of 2D-images 2 are in this example six 2D-images, which all lie in the single 2D-representation-surface. The six 2D-images are stitched together using an image fusion algorithm. Further, the set of 2D-images are recorded in the second recording mode that is based on illuminating the tooth with light in the visible domain.

Example 3—a User-Interface

Figure 3:
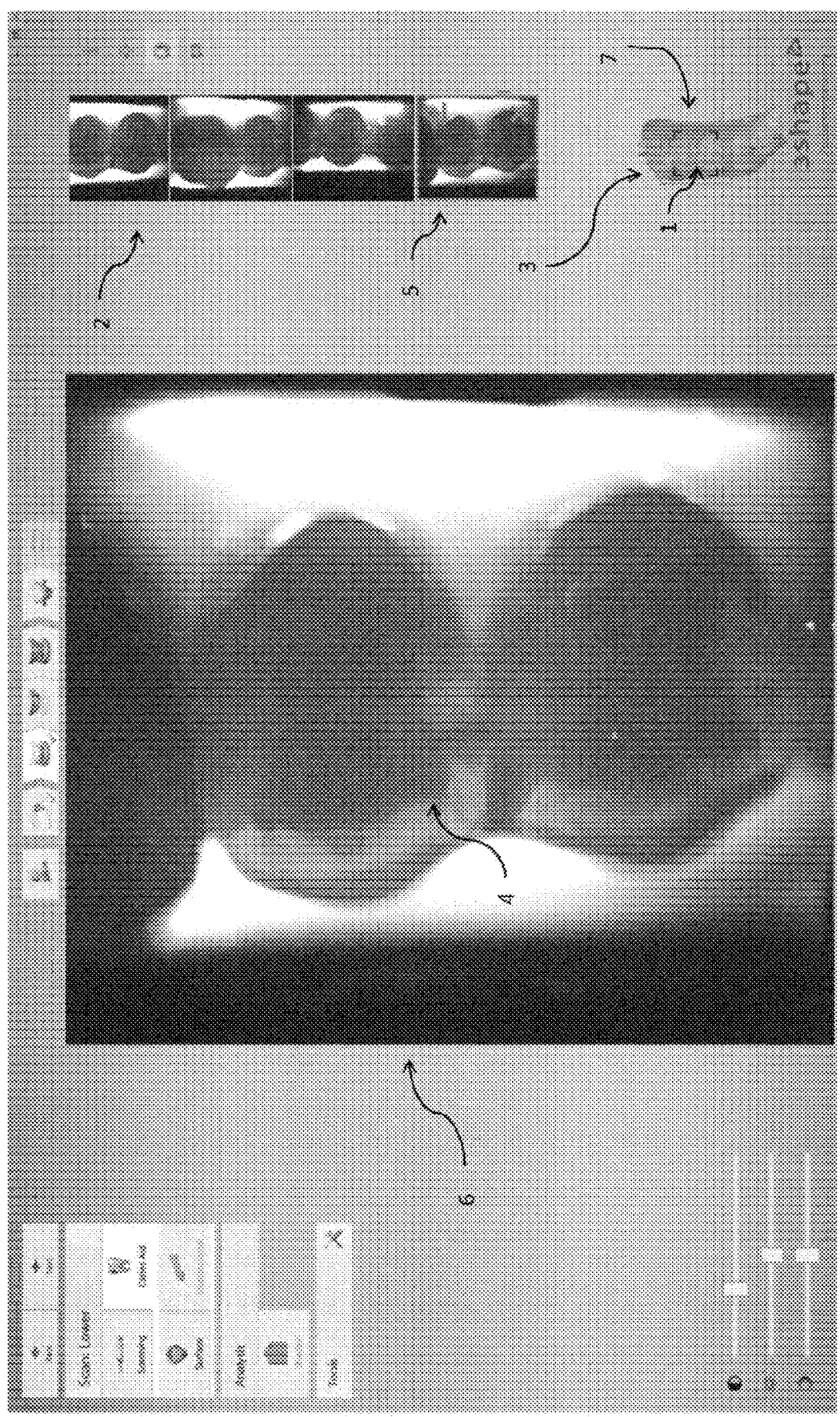
FIG. 3 shows an example of a user-interface.

FIG. 3 shows an example of user-interface according to the present invention.

The user-interface (UI), here a graphical user-interface, is based on a computer-implemented method for correlating at least one infrared 2D-image to a 3D-representation 3 of at least a part of a tooth 4 and displayed. In other words, the user-interface displays the correlation. Further, the user-interface is in communication with a hand-held scanning device and the UI is displayed on a screen. The correlation, as displayed in the UI, is obtained by the following steps.

First, the UI, or the computer-implemented method, i.e. the algorithm, obtains (by receiving from a handheld device) a first set of 2D-images of the at least part of the tooth 4. This first set of 2D-images is acquired by the hand-held scanning device using white light. The handheld device transfers the image data to a processing device, whereon the algorithm reads the image data.

Secondly, the UI then forms a 3D-representation 3 of the at least a part of the tooth 4 from the first set of 2D-images. This 3D-representation is then displayed in the UI.

Thirdly, the UI obtains (by receiving from a handheld device) a second set of 2D-images 2 of the at least part of the tooth 4. This second set of 2D-images 2 is acquired by the hand-held scanning device using infrared light. Accordingly, the second set of 2D images 2 is infrared 2D-images acquired within the at least part of the tooth 4. The handheld device transfers the image data to a processing device, whereon the algorithm reads the image data. At least one of the 2D-images from the second set of 2D-images 2 is displayed in the UI. In this example, four of the infrared 2D-images 2 are displayed in the UI.

Fourthly, the UI displays a manipulator 5 configured to change between the infrared 2D-images in the second set of 2D-images 2. The user is able to change between the 2D-images in the second set of 2D-images 2 until a desired 2D-image 6 is displayed. In other words, the user can move the manipulator 5. Based on the position of the manipulator 5, and because the UI receives input as associated to the manipulator 5, here the position of the manipulator 5, the infrared 2D-images are changed as a function of the position of the manipulator 5.

Finally, the UI displays how the desired 2D-image 6 is correlated to the 3D-representation 3. The correlation itself has continuously been made by the computer implemented method running in the background of the UI as the first set of images and second set of images are acquired. The manipulator 5 displayed in the graphical user-interface is in the form of a scrollbar. In this example, the scroller or the scroll box inside the track of the scrollbar is in the form location-indicator to show images from selected positions inside the tooth 4. In this example, a correlation-indicator 7 shows the location of where the desired 2D-image 6 relates and/or correlate to the 3D-representation 3.

As previously described, the step of correlating the desired 2D-image 6 to the 3D-representation 3 is represented in the user-interface such that only the desired image 2D-image 6 is shown in relation to the 3D-representation 3 of the at least a part of the tooth 4.

In the UI, both the 2D-image (the desired infrared 2-image 6) of inside the tooth 4 and the 3D-representation 3 are displayed as two separate representations. However, the two separate representations are combined in a combined 2D/3D-representation by the correlation, here combined with the manipulator 5 and the correlation-indicator 7. By moving the manipulator 5, the correlation-indicator 7 is moved correspondingly. It also works the other way around—by moving the correlation indicator 7, the manipulator 5 is also moved correspondingly. Thus, in this example, the correlation-indicator 7 is configured like the manipulator 5. In other words, the correlation-indicator 7 is also configured to change between the infrared 2D-images in the second set of 2D-images 2. Thus, the correlation-indicator 7 is another manipulator 5.

Accordingly, the combined 2D/3D-representation comprises the 3D-representation 3 correlated with the at least one 2D-image 6 in a single 2D-representation-surface 1 within the 3D-representation 3.

Due to the correlation, each tooth 4 or the at least part of the tooth 4 in the 3D-representation 3 uniquely identifies the second set of images 2 belonging to the respective tooth 4 or the at least part of the tooth 4. Thus, when a tooth 4 or the at least part of the tooth 4 in the 3D-representation 3 is selected in the user-interface (using the correlation indicator 7), the second set of 2D-images 2 acquired within the tooth or within the at least part of the tooth is displayed as an image-by-image 6 in the user-interface.

In this example here presented, the second set of 2D-images 2 is a focus-stack of 2D-images recorded along a single 2D-physical surface.

Further details are described by the below items:

Items:
1. A computer-implemented method for correlating at least one additional 2D-image to a 3D-representation of at least a part of a tooth, comprising the steps of:
   obtaining a first set of 2D-images, wherein the first set of 2D-images are recorded in a first recording mode using a hand-held device;
   forming a 3D-representation of the at least a part of the tooth from the first set of 2D-images;
   defining a single 2D-representation-surface within the 3D-representation;
   obtaining at least one additional 2D-image, wherein the at least one 2D-image is recorded in a second recording mode different from the first recording mode using the hand-held device; and
   correlating the at least one 2D-image to the 3D-representation such that the at least one 2D-image lies in the single 2D-representation-surface in the 3D-representation, thereby obtaining a combined 2D/3D-representation, the combined 2D/3D-representation comprising the 3D-representation correlated with the at least one 2D-image only in the single 2D-representation-surface within the 3D-representation.
2. The method according to item 1, wherein the step of defining the single 2D-representation-surface is performed before the step of correlating the at least one additional 2D-image to the 3D-representation.
3. The method according to item 1, wherein the step of defining the single 2D-representation-surface is performed after the step of correlating the at least one additional 2D-image to the 3D-representation.
4. The method according to any of the previous items, wherein the single 2D-representation-surface is a planar surface.
5. The method according to any of the items 1-3, wherein the single 2D-representation-surface is a curved surface.
6. The method according to any of the previous items, wherein the single 2D-representation-surface is an intersection-surface through the 3D-representation of the at least a part of the tooth.
7. The method according to any of the previous items, wherein the single 2D-representation-surface is re-defined based on input from a user-interface or input from the hand-held device.
8. The method according to any of the previous items, wherein the step of defining the single 2D-representation-surface is based on spanning a fitting-surface relative to the 3D-representation of at least part of the tooth, preferably relative to the cusp of the 3D-representation of at least said tooth.
9. The method according to item 8, wherein the fitting-surface is determined by a least-square algorithm.
10. The method according to any of the previous items, wherein the step of defining the single 2D-representation-surface is based on selecting a focal plane within the first set of 2D-images.
11. The method according to item 10, wherein the step of selecting the focal-plane is based on input from a user-selected 2D image.
12. The method according to any of the previous items, wherein the step of obtaining at least one additional 2D-image is based on the at least one additional 2D-image being recorded after and/or before at least one 2D image in the first set of 2D-images being recorded in the first recording mode.
13. The method according to any of the previous items, wherein the at least one additional 2D-image is a second 2D-image or a set of second 2D-images, such as a focus-stack of 2D images recorded perpendicular to a single 2D-physical-surface corresponding to the single 2D-representation-surface, and/or such as a series of 2D images recorded along a single 2D-physical-surface corresponding to the single 2D-representation-surface.
14. The method according to item 13, wherein the single 2D-representation surface is fitted to the position and orientation of the images in the second set of 2D images.
15. The method according to item 13, wherein the step of obtaining at least one additional 2D-image is based on filtering the second set of 2D images.
16. The method according to any of the previous items, wherein the step of obtaining at least one additional 2D-image is based on the at least one additional 2D-image being recorded when the hand-held device is focused within a selected distance from a single 2D-physical surface corresponding to the single 2D-representation-surface.
17. The method according to any of the previous items, wherein the step of obtaining at least one additional 2D-image is based on the at least one additional 2D-image being recorded when the hand-held device is focused within a selected angular position a single 2D-physical surface corresponding to the single 2D-representation-surface.
18. The method according to any of the previous items, wherein the step of correlating the at least one additional 2D-image to the 3D-representation is based on projecting the at least one 2D-image to the single 2D-representation-surface within the 3D-representation.
19. The method according to any of the previous items, wherein the step of correlating the at least one additional 2D-image to the 3D-representation further comprises obtaining a second set of 2D-images and stitching said 2D-images in the 2D-representation-surface using an image fusion algorithm.
20. The method according to any of the previous items, wherein the first recording mode is based on illuminating the tooth with light in the visible domain, preferably with one or more wavelengths in the range between 400 nm to 700 nm, more preferably in the range between 400 nm to 600 nm.
21. The method according to the items 1-19, wherein the first recording mode comprises a step of illuminating the tooth with light in the ultraviolet domain.

22. The method according to any of the previous items, wherein the second recording mode is based on illuminating the tooth with light in the infrared domain, preferably with one or more wavelengths in the range between 700 nm to 2500 nm, more preferably in the range between 800 nm to 1000 nm, most preferably around 850 nm.
23. The method according to items 1-21, wherein the second recording mode is based on illuminating the tooth with light in the visible domain, preferably with one or more wavelengths in the range between 600 nm to 700 nm.
24. The method according to any of the previous items, further comprising a step of displaying the combined 2D/3D-representation on a screen.
25. A processing unit for correlating at least one additional 2D-image to a 3D-representation of at least a tooth, wherein the processing unit is configured for performing the computer implemented method according to item 1.
26. The processing unit according to item 25, wherein the processing unit is configured for performing the computer implemented method according to any of the items 2-24.
27. A 2D/3D-scanning-system for correlating at least one additional 2D-image to a 3D-representation of at least a part of a tooth, comprising:
    a hand-held device comprising:
        at least a first light source configured for transmitting light in a first optical domain and light in a second optical domain,
        a detector configured for recording 2D-images,
        wherein the hand-held device is configured for being operated in at least two recording modes:
        a first recording mode, wherein a first set of 2D-images are recorded onto the detector by illumination of light in the first optical domain,
        a second recording mode, wherein the at least one additional 2D-image is recorded onto the detector by illumination of light in the second optical domain; and
    the processing unit according to any of the items 25-26.
28. The 2D/3D scanning system according to item 26, wherein the processing unit is located external to the hand-held device, such as located in a separate computer.
29. The 2D/3D scanning system according to any of the items 262-28, wherein the first optical domain is in the visible domain, preferably with one or more wavelengths in the range between 400 nm to 700 nm, more preferably in the range between 400 nm to 600 nm.
30. The 2D/3D scanning system according to any of the items 2627-28, wherein the first optical domain is in the domain from 350 nm to 430 nm.
31. The 2D/3D scanning system according to any of the items 262-30, wherein the second optical domain is in the infrared domain, preferably with one or more wavelengths in the range between 700 nm to 2500 nm, more preferably in the range between 800 nm to 1000 nm, most preferably around 850 nm.
32. The 2D/3D scanning system according to any of the items 26, wherein the second optical domain is in the visible domain, preferably with one or more wavelengths in the range between 600 nm to 700 nm.
33. The 2D/3D scanning system according to any of the items 26, wherein the at least first light source is a first light source and a second light source.
34. The 2D/3D scanning system according to any of the items 26, wherein the at least one additional 2D-image being recorded after and/or before at least one 2D image in the first set of 2D-images being recorded in the first recording mode.
35. The 2D/3D scanning system according to any of the items 26, the hand-held device further comprising an aperture optically connected to the detector, the aperture comprising an outer annular disc configured for blocking the light in the second optical domain, such that the at least one additional 2D-image is recorded with extended depth-of-field compared to the first set of images recorded in the first recording mode.
36. A computer-implemented method for correlating at least one additional 2D-image to a 3D-representation of at least a part of a tooth displayed in a graphical user-interface on a screen, comprising the steps of:
    obtaining a first set of 2D-images, wherein the first set of 2D-images are recorded in a first recording mode using a hand-held device;
    forming a 3D-representation of the at least a part of the tooth from the first set of 2D-images in the graphical user-interface;
    defining a single 2D-representation-surface within the 3D-representation using a manipulator displayed in the graphical user-interface;
    obtaining at least one additional 2D-image, wherein the at least one 2D-image is recorded in a second recording mode different from the first recording mode using the hand-held device; and
    based on input as provided by the manipulator, correlating the at least one 2D-image to the 3D-representation such that the at least one 2D-image lies in the single 2D-representation-surface in the 3D-representation, thereby obtaining a combined 2D/3D-representation, the combined 2D/3D-representation comprising the 3D-representation correlated with the at least one 2D-image only in the single 2D-representation-surface within the 3D-representation.
37. A computer-implemented method for correlating at least one additional 2D-image to a 3D-representation of at least a part of a tooth displayed in a graphical user-interface on a screen, comprising the steps of:
    obtaining a first set of 2D-images, wherein the first set of 2D-images are recorded in a first recording mode using a hand-held device;
    forming a 3D-representation of the at least a part of the tooth from the first set of 2D-images in the graphical user-interface;
    defining a single 2D-representation-surface within the 3D-representation;
    obtaining at least one additional 2D-image, wherein the at least one 2D-image is recorded in a second recording mode different from the first recording mode using the hand-held device;
    correlating the at least one 2D-image to the 3D-representation such that the at least one 2D-image lies in the single 2D-representation-surface in the 3D-representation, thereby obtaining a combined 2D/3D-representation, the combined 2D/3D-representation comprising the 3D-representation correlated with the at least one 2D-image only in the single 2D-representation-surface within the 3D-representation;
    re-defining the single 2D-representation-surface within the 3D-representation using a manipulator displayed in the graphical user-interface; and based on input as provided by the manipulator, re-correlating the at least one 2D-image to the 3D-representation.

The invention claimed is:

1. A computer-implemented method for correlating at least one infrared 2D-image to a 3D-representation of at least a part of a tooth displayed in a graphical user-interface, of a hand-held scanning device, on a screen, comprising the steps of:
    obtaining a first set of 2D-images of the at least part of the tooth;
    forming a 3D-representation of the at least a part of the tooth from the first set of 2D-images;
    displaying, in the graphical user-interface, the 3D-representation;
    obtaining a second set of 2D-images, wherein the second set of 2D images are infrared 2D-images acquired within the at least part of the tooth;
    displaying, in the user-interface, at least one of the 2D-images from the second set of 2D-images;
    displaying, in the user-interface, a manipulator configured to change between 2D-images in the second set of 2D-images;
    based on input as associated to the manipulator, changing between the 2D-images in the second set of 2D-images until a desired 2D-image is displayed; and
    correlating the desired 2D-image to the 3D-representation.

2. The method according to claim 1, wherein the step of correlating the desired 2D-image to the 3D-representation is based on comparing information in the first set of images with information in the second set of images.

3. The method according to claim 2, wherein the information is related to the acquisition-time of the images.

4. The method according to claim 1, wherein the step of correlating the desired 2D-image to the 3D-representation is represented in the user-interface such that only the desired 2D-image is shown in relation to the 3D-representation of the at least a part of the tooth.

5. The method according to claim 1, wherein the step of correlating the desired 2D-image to the 3D representation is represented in the user-interface as a combined 2D/3D-representation.

6. The method according to claim 5, wherein the combined 2D/3D-representation comprises two separate datasets linked together by the correlation such that the combined 2D/3D-representation further comprises two separate representations.

7. The method according to claim 5, wherein the combined 2D/3D representation comprises a single dataset obtained by correlating two separate datasets.

8. The method according to claim 1, wherein the step of forming the 3D-representation is such that each tooth or the at least part of the tooth in the 3D-representation uniquely identifies a second set of images belonging to the respective tooth or the at least part of the tooth.

9. The method according to claim 1, wherein the second set of 2D-images is a focus-stack of 2D-images recorded along a perpendicular axis with respect to a single 2D-physical-surface.

10. The method according to claim 1, wherein the second set of 2D-images is a focus-stack of 2D-images recorded along a single 2D-physical surface.

11. The method according to claim 1, wherein the manipulator displayed in the graphical user-interface is a scrollbar and/or a location-indicator to show images from selected positions and/or orientations.

12. The method according to claim 1, wherein the manipulator displayed in the graphical user-interface is based on clicking on the 2D-image and wherein the desired image is obtained by moving a cursor, by touch input on the screen, or by using the hand-held scanning device.

13. The method according to claim 1, wherein the step of obtaining a second set of 2D-images is based on filtering the second set of 2D images.

14. The method according to claim 1, wherein the infrared images are obtained by, in the user-interface, selecting that the handheld scanning device is operating with one or more wavelengths in the range between 700 nm to 2500 nm.

15. A handheld scanning device in communication with the graphical user-interface according to claim 1.

* * * * *